US00PP34488P3

(12) United States Plant Patent
Schurr

(10) Patent No.: US PP34,488 P3
(45) Date of Patent: Aug. 9, 2022

(54) ***HAEMATOCOCCUS* MICROALGA NAMED 'KAS1601-WG7'**

(50) Latin Name: ***Haematococcus pluvialis* (syn. *H. lacustris*)/*microalga*.**
Varietal Denomination: KAS1601-WG7

(71) Applicant: Kuehnle AgroSystems, Inc., Honolulu, HI (US)

(72) Inventor: Robert J. Schurr, Honolulu, HI (US)

(73) Assignee: Kuehnle AgroSystems, Inc., Honolulu, HI (US)

( * ) Notice: Subject to any disclaimer, the term of this patent is extended or adjusted under 35 U.S.C. 154(b) by 0 days.

(21) Appl. No.: 17/085,405

(22) Filed: Oct. 30, 2020

(65) Prior Publication Data

US 2022/0142031 P1 May 5, 2022

(51) Int. Cl.
*A01H 13/00* (2006.01)

(52) U.S. Cl.
USPC ..... Plt./395

(58) Field of Classification Search
USPC ..... Plt./395
CPC ..... A01H 13/00; C12N 1/12; C12N 1/125; C12P 5/00; C12R 2001/89
See application file for complete search history.

(56) References Cited

U.S. PATENT DOCUMENTS

2008/0038774 A1 2/2008 Higashiyama et al.
2018/0002711 A1 1/2018 Schurr et al.

OTHER PUBLICATIONS

"Analysis of Natural Astaxanthin Derived from *Haematococcus* Microalgae in Astaxanthin Oleoresin, Astaxanthin Gelcaps, Astaxanthin Beadlets, and *Haematococcus* Biomass," *Cyanotech*, Mar. 15, 2013, pp. 1-22.
Shah, M. M. R. et al., "Astaxanthin-Producing Green Microalga *Haematococcus pluvialis*: From Single Cell to High Value Commercial Products," *Frontiers in Plant Science*, Apr. 28, 2016, 7:1-28.

*Primary Examiner* — June Hwu
(74) *Attorney, Agent, or Firm* — Saliwanchik, Lloyd & Eisenschenk

(57) ABSTRACT

A novel variety of the microalga *Haematococcus pluvialis* (syn. *H. lacustris*), named 'KAS1601-WG7' is primarily characterized by a yellow and motile cell body during propagation transitioning to a red and motile cell body under pigment accumulation conditions. The cells contain negligible chlorophyll. It has fast growth under heterotrophic cultivation for ease of propagation and shows high carotenogenesis under dark heterotrophic cultivation. The highly pigmented non-encysted cells are attractive for ease of extraction and for high digestibility, including as whole cells, to release a mixture of oils, proteins, pigments, and other components desirable for use in food, feeds, cosmetics and dietary supplements, and excellent storage as biomass.

4 Drawing Sheets

Latin name: *Haematococcus pluvialis* (syn. *H. lacustris*)/microalga.

Varietal denomination: 'KAS1601-WG7'.

BACKGROUND OF THE INVENTION

The unicellular, photosynthetic, biflagellate green microalga *Haematococcus pluvialis* Flotow (class Chlorophyceae) has a cosmopolitan distribution generally in transient, freshwater habitats. A summary of the alga's biology is found in Shah et al. (2016). Wild-type *H. pluvialis* has a "green vegetative phase" characterized by green, ovoid, motile (flagellated) macrozooid cells and green, spherical, non-motile (non-flagellated) palmella cells. The carotenoid fraction of green vegetative cells of wild-type *H. pluvialis* consists largely of the yellow/orange pigments lutein (75-80%) and β-carotene (10-20%). Vegetative cells are green due to chlorophyll as the dominant pigment, masking the carotenoid colors.

Wild-type *H. pluvialis* cells transition under sustained unfavorable environmental or laboratory culture conditions (such as nutrient deprivation, high light irradiance, high temperature, and/or high salinity) to a "red encysted phase"

characterized by red, enlarged, spherical, non-motile aplanospores (hematocysts). Carotenoid content of hematocysts is notably elevated compared to that of green vegetative cells and is dominated by the red pigment astaxanthin (80-99% of total carotenoids). The period of time required for encystment and accumulation of astaxanthin is typically 7-10 days (168-240 hours). The cell size of cysts is almost double that of macrozooids, the latter being generally between 8 and 20 μm long.

Strains that exemplify *H. pluvialis* and synonymous *H. lacustris* are listed in U.S. Patent Application Publication No. 2008/0038774. 'NIES-144' cells (sized 15 μm minimum to 35 μm maximum) have been cultivated through both the vegetative and encysted phases under dark heterotrophic conditions with acetate as the carbon source in the liquid culture medium. The green vegetative cells require encystment to induce astaxanthin accumulation in the dark over 8 days, accomplished under elevated salinity and temperature, as described in U.S. Patent Application Publication No. 2008/0038774.

Commercially, *H. pluvialis* is widely cultivated in raceways or photobioreactors under sunlight or other forms of illumination in the "green vegetative phase" and then stressed to transition to the "red encysted phase" to produce hematocysts with 1.5% w/w astaxanthin content (for use in aquafeeds) or higher astaxanthin content (for use in multiple markets). Hematocysts are characterized by thick rigid cell walls that must be broken open to access the pigments for extraction, product formulation, or bioavailability.

BRIEF SUMMARY OF THE INVENTION

The invention relates to a new and distinct cultivar of *Haematococcus*, botanically known as *Haematococcus pluvialis* (synonym *H. lacustris*), and hereinafter referred to by the cultivar name 'KAS1601-WG7'.

The new microalga 'KAS1601-WG7' is a product of the microalga breeding program in Honolulu, HI. It was discovered and selected during August 2019 in Honolulu, HI. in a cultivated area of microalga cultures being propagated in the laboratory of a fermentation facility under conditions of heterotrophy. It arose as a naturally occurring sport of unknown causation from a facultative heterotrophic parent green cell line. The origin parent is known as 'KAS1601' (described in U.S. Patent Application Publication No. 2018/0002711), a commercial variety of *Haematococcus* that also arose as a sport. The new microalga 'KAS1601-WG7' was subsequently asexually reproduced on the facilities of Kuehnle AgroSystems in Honolulu, HI. by the inventor, a research scientist. The reproduction techniques used were clonal propagation through cell colony selection, plating onto solidified culture medium, and liquid cell culture. All propagations of the new cultivar have been true to type in cell characteristics during propagation culture and in pigment accumulation culture, demonstrating that the combination of characteristics as herein disclosed are maintained through successive generations.

The asexually reproduced new cultivar has several desirable commercial characteristics, including fast growth under heterotrophic cultivation, ease of propagation, yellow culture with negligible chlorophyll transitioning to red culture as motile non-encysted cells attractive for ease of extraction and for digestion as whole cells, rapid high pigments accumulation under dark heterotrophic cultivation, a mix of pigments profile desirable for use in food, feeds, cosmetics and dietary supplements, and excellent storage as biomass.

The following combination of traits distinguishes 'KAS1601-WG7' as a new cultivar:

1. The yellow culture, approximately Pantone Formula Guide 393 U, produced under vegetative heterotrophic propagation conditions of replete nutrients. This differs from the green culture of other *H. pluvialis* and the parent 'KAS1601', approximately Pantone Formula Guide 374 U, when produced under the same conditions.
2. The red biomass, approximately Pantone Formula Guide 7593 U when dried into a powder, produced under pigment accumulation conditions of deplete nutrients. This differs from the more maroon biomass of the parent 'KAS1601' approximately Pantone Formula Guide 1817 U, when produced under the same conditions.
3. The yellow or the red cell body size is about 16 microns long and about 13 microns wide. These dimensions are like those of the parent 'KAS1601', as both strains remain as motile non-encysted cells during astaxanthin accumulation. In contrast, red macrozooids of 'KAS1601-WG7' have a cell body width that is about 2.5× smaller than red cysts of wild-type *H. pluvialis* of about 33 microns.
4. Pigment extracted from biomass comprised of red motile cells and separated on a thin layer chromatograph or by high pressure liquid chromatography reveals that the new variety accumulates astaxanthin in the form of monoesters (about 75%), diesters (about 22%), and free astaxanthin (about 3%) comprising about 90% of total pigment. This chemistry is like that of other *H. pluvialis* and the parent 'KAS1601', but differs by originating from non-encysted red motile cells compared to that from wild-type *H. pluvialis* that originates from red cysts.
5. Pigment extracted from biomass comprised of red motile cells and separated on a thin layer chromatograph or by HPLC reveals that the new variety accumulates xanthophylls and carotenoids other than astaxanthin comprising lutein (about 52%), beta-carotene (about 40%), zeaxanthin (about 6%), and canthaxanthin (about 2%). This chemistry is similar to the parent 'KAS1601' but with much less chlorophyll present. Other *H. pluvialis* do not produce red motile cells.
6. Micropropagation using cell suspension methods in dark heterotrophic culture is fast, with a sustained growth rate exceeding 0.7/d or even 0.8/d. This differs from other *H. pluvialis* which grows heterotrophically at a much slower rate of about 0.22/day on acetate. Astaxanthin accumulation is rapid, in 72 hours or even 48 hours or less in the dark, well over twice as fast as strain 'NIES-144' in the dark.

BRIEF DESCRIPTION OF THE DRAWINGS

The new cultivar is illustrated by the accompanying color photographs in which.

Figure 1:
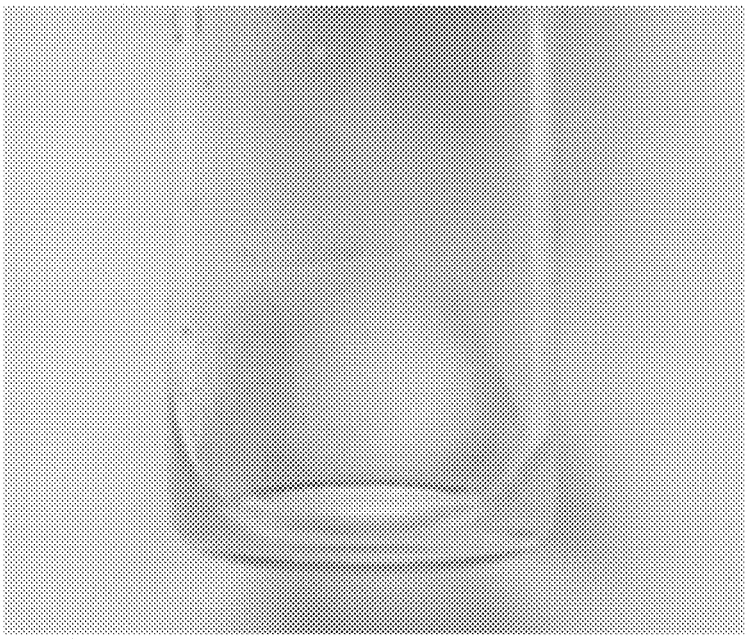
FIG. 1 shows a representative yellow liquid culture of the new cultivar under nutrient replete cultivation.
Figure 2:
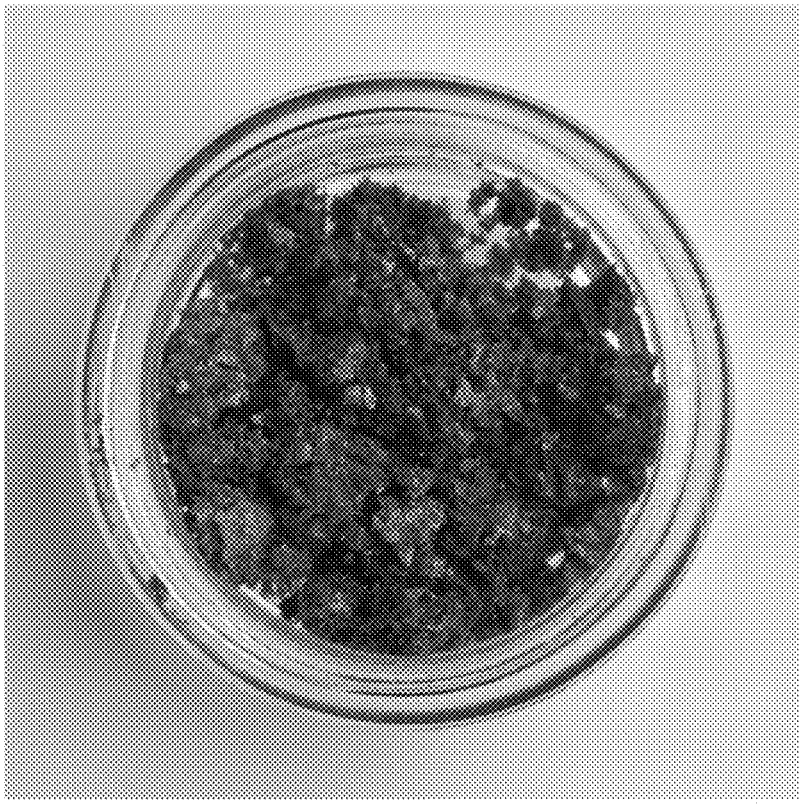
FIG. 2 shows a representative red dried biomass from a carotenogenic cell culture that arose from a yellow culture once under nutrient deplete cultivation.
Figure 3:
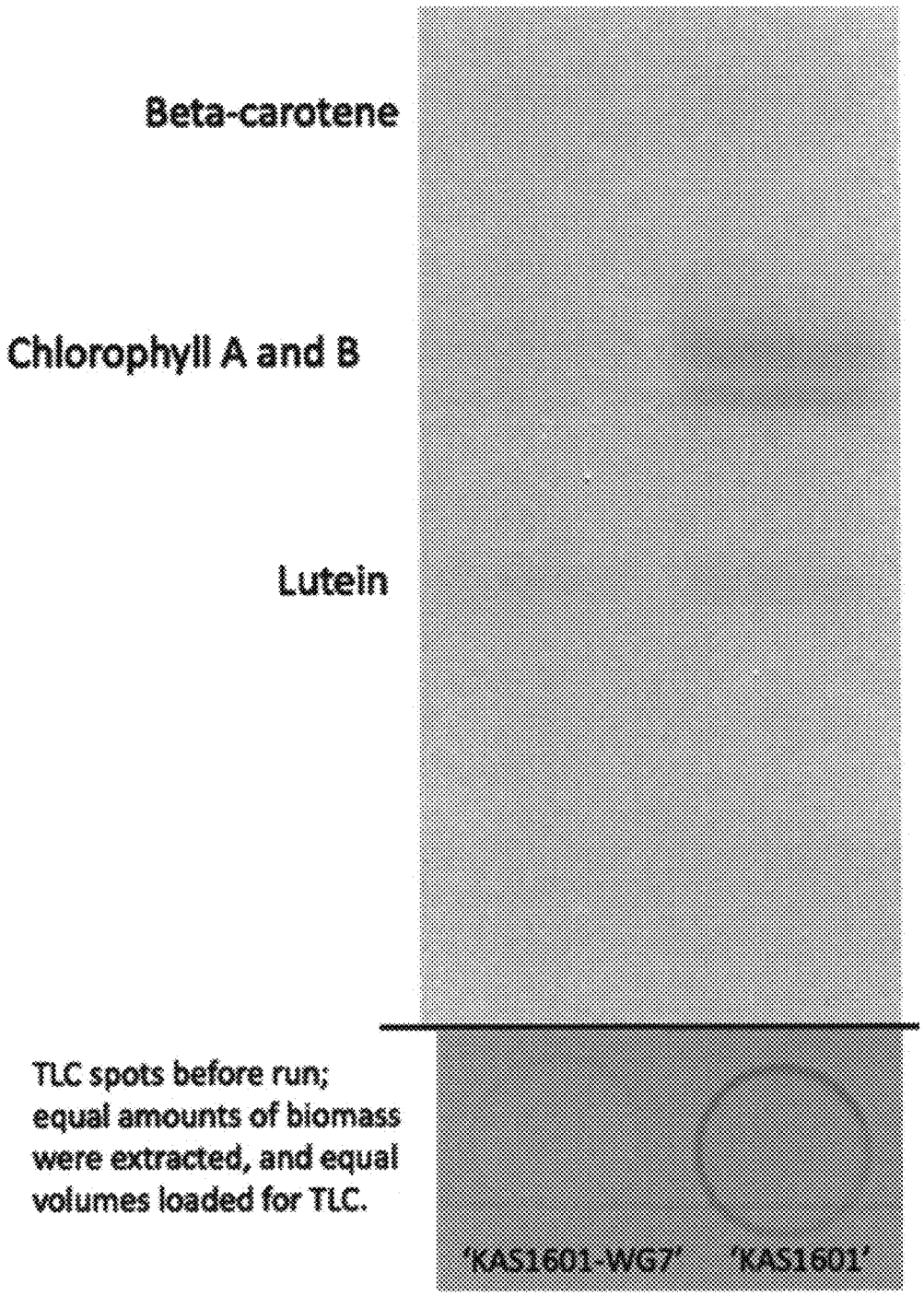
FIGS. 3 and 4 show new microalga *Haematococcus pluvialis* 'KAS1601-WG7', during active cell division, produces yellow biomass with much lower chlorophyll content than the parent *H. pluvialis* 'KAS1601', which produces green biomass, as seen in FIG. 3, thin layer chromatography (TLC) with negligible green chlorophyll bands; and in FIG. 4, a spectral scan of ethanolic extracts of equal amounts of vegetative biomass from 'KAS1601-WG7' (red triangles) and parent 'KAS1601' (green circles), with optical density (OD) measured between 650-700 nm wavelengths to show absorption by chlorophyll with no interference from carotenoids.
Figure 4:
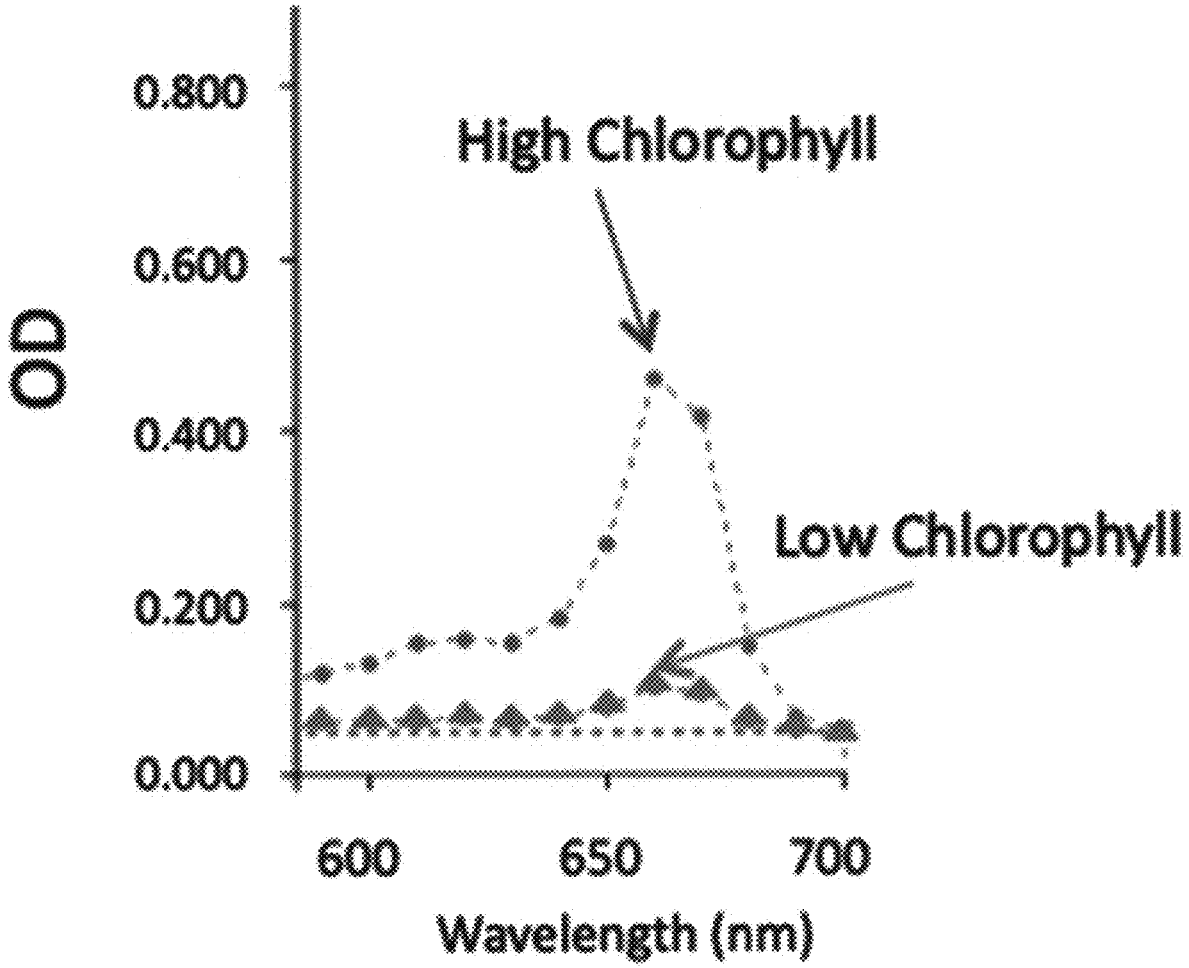

The colors are as accurate as is reasonably possible with color illustrations of this type.

DETAILED DISCLOSURE OF THE INVENTION

The novel variety 'KAS1601-WG7' was identified as a single red colony growing in the dark on an agar plate of 'KAS1601' green colonies. The red colony was streaked to a new agar plate and again grew red in the dark. The red streak was transferred to liquid medium and grew up as "white", very pale cells when viewed under the microscope. When concentrated and dried, the biomass appears yellow. This liquid culture, after a few subcultures, was stressed (deplete in urea nitrogen) and then single cell sorted to generate the 'KAS1601-WG7' isolate.

Heterotrophic culture is in liquid medium, with growth conditions as shown in Table 1. To enable carotenogenesis to produce astaxanthin-rich red biomass in the vegetative motile cells, the culture medium is depleted of nitrogen in the presence of replete carbon, with other nutrients and culture conditions, as described in U.S. Patent Application No. 2018/0002711. While any number of harvesting methods as known in the art can be used for the new microalga, the data presented is based on continuous centrifugation. No cell disruption by milling or cracking is done; biomass is comprised of thin-walled, vegetative, non-encysted cells. While any number of dehydration methods as known in the art can be used for the new microalga, the data presented are based on lyophilization. The pigment data presented are based on solvent extraction using ethanol (5 mg biomass per mL ethanol) for thin layer chromatography or using DMSO without the use of glass beads for high pressure liquid chromatography (Cyanotech 2013). Stability of stored biomass is greater than 24 months frozen at −20° C., at 5% moisture content, with about 10% loss of pigments.

TABLE 1

Heterotrophic culture is in liquid medium for cultivation of 'KAS1601-WG7'.

| Light | Temperature | pH | Carbon source in medium | Nutrients | Life cycle stages during cultivation |
|---|---|---|---|---|---|
| None, complete darkness | 25° C. | 7.2 in flask; 7.0-7.8 in fermentor | Acetate ion | As described in U.S. patent application No. 20180002711 | Vegetative cells only, not encysted |

The following observations, measurements and values describe the new cultivar grown in Honolulu, HI., under full darkness, conditions which closely approximate those generally in use for commercial fermentation production of microalga. This includes a carbon source, macro and micronutrients, and temperature and oxygenation conditions conducive to cell division.

Origin:

*Source*.—'KAS1601' (U.S. Patent Application Publication No. 20180002711), aseptically cultivated by tissue culture in freshwater medium in complete darkness since 2015. It propagates asexually as a green chlorophyllic vegetative cell colony or suspension maintained as a facultative heterotroph in the dark. The cell suspension color is bright green (approximately Pantone Formula Guide 374 U) at low density; the observed shade of green will vary depending on culture cell density (appearing darker green at higher densities above 1 g/L) and on size of the vessel containing the observed culture. The resulting dried biomass obtained from a carotenogenic cell culture grown under stress from nutrient depletion in complete darkness is dark red similar to burnt umber (approximately Pantone Formula Guide 1817 U) due to the presence of both carotenoids and chlorophylls.

*Sport*.—'KAS1601-WG7', aseptically cultivated by tissue culture in freshwater medium in complete darkness since 2019. It propagates asexually as a yellow cell suspension maintained as a facultative heterotroph in the dark. The sport was identified in a heterogeneous colony in August 2019 and purified away from green cells through successive replating to obtain a homogeneous yellow line in liquid culture in September 2019.

Classification: *Haematococcus pluvialis* 'KAS1601-WG7'.

*Trophic capability*.—Facultative heterotroph.

*Cell form*.—Vegetative cells generally spherical to ovoid. Papillae absent, cell membrane hyaline. Chloroplast cup-shaped, occupying about ⅓ of the protoplast.

*Cell size*.—Vegetative cells generally spherical to ovoid, average 16 micron long (range 12-18 micron), 13 micron wide (range 10-15 micron), with a length: width difference of about 3 micron.

*Flagella*.—Two isokont anterior flagella present, length as long as the cell.

*Color*.—As vegetative cells under nutrient replete conditions, a liquid cell suspension culture appears yellow (approximately Pantone Formula Guide 393 U), indicating negligible chlorophyll. The resulting dried biomass obtained from a carotenogenic cell culture grown under stress of nutrient depletion in complete darkness is red, similar to burnt sienna (approximately Pantone Formula Guide 7593 U). The red biomass containing carotenoids has an indiscernible amount of chlorophyll providing a purer carotenoid product.

*Pigment accumulation*.—Carotenogenesis occurs as a motile ovoid cell under complete darkness following the conditions described in U.S. Patent Application Publication No. 2018/0002711. Cells do not require encystment in order to accumulate high levels of pigment. Cells retain their flagella. As motile cells under pigment accumulation conditions, the liquid cell suspension culture appears red, producing a red dried biomass (approximately Pantone Formula Guide 7593 U). The extracted pigments separated on a thin layer chromatograph and by HPLC reveal that the new variety has astaxanthin present along with lutein, beta-carotene, zeaxanthin, and canthaxanthin. Total astaxanthin can exceed 2.5% by weight and can accumulate in 72 hours or less.

*Reproduction*.—Vegetative. Sexual reproduction features not systematically observed but not believed to differ from those of other cells within the species.

*Fecundity*.—The growth rate in dark fermentation under nutrient replete conditions exceeds 0.7/d or even 0.8/d.

Nutrient metabolism: 'KAS1601-WG7' is capable of metabolizing nitrogen in multiple forms in heterotrophic culture, including but not limited to the forms of urea, nitrate, ammonium, and yeast extract.

General observations: 'KAS1601-WG7' is a stable yellow cell sport derived from a green parent cell. Morphologically it is similar to the origin parent in cell size and shape during cultivation. It also shares similar astaxanthin esters and carotenoid composition with the origin parent. Cells in environmentally stressed culture turn red highlighted by no loss of flagella and the absence of encystment, the latter occurring only rarely. The lack of encystment is attractive for ease of extraction and for high digestibility due to lack of a rigid cyst wall. The yellow variety has excellent growth rate (0.7/d or greater), with an astaxanthin content exceeding 2.5% when cultivated under stress conditions. 'KAS1601-WG7' is especially desirable because of its indiscernible chlorophyll, fast growth, high pigment yield, dark heterotrophic growth, and ability to accumulate pigments by carotenogenesis in the dark and without encystment. Due to its unique combination of characteristics, 'KAS1601-WG7' provides an excellent new *Haematococcus pluvialis* cultivar for commercial cropping.

LITERATURE CITED

1. M. M. R. Shah, Y. Liang, J. J. Cheng, and M. Daroch. 2016. Astaxanthin-Producing Green Microalga *Haematococcus pluvialis*: From Single Cell to High Value Commercial Products. doi: 10.3389/fpls.2016.00531
2. Cyanotech. 2013. Analysis of Natural Astaxanthin Derived from *Haematococcus* Microalgae in Astaxanthin Oleoresin, Astaxanthin Gelcaps, Astaxanthin Beadlets, and *Haematococcus* Biomass (Mar. 15, 2013), section 8.03.
3. U.S. Patent Application Publication No. 2008/0038774.
4. U.S. Patent Application Publication No. 2018/0002711 now U.S. Pat. No. 11,034,968.

I claim:

1. A new and distinct variety of the microalga *Haematococcus pluvialis* (syn. *H lacustris*) variety 'KAS1601-WG7', substantially as described and illustrated, which is characterized by the combined features of yellow, motile, flagellated, vegetative cell capable of forming a red motile flagellated cell to produce a red biomass.

* * * * *